United States Patent [19]
Harrison

[11] Patent Number: 4,823,813
[45] Date of Patent: Apr. 25, 1989

[54] ELECTROSTATIC DEEP HEATING APPLICATORS

[76] Inventor: William H. Harrison, 32180 Mulholland Dr., Malibu, Calif. 90265

[21] Appl. No.: 52,246

[22] Filed: May 19, 1987

Related U.S. Application Data

[63] Continuation-in-part of Ser. No. 6,219, Jan. 23, 1987.

[51] Int. Cl.⁴ .............................................. A61N 1/40
[52] U.S. Cl. .................................. 128/804; 219/10.81
[58] Field of Search ................................ 128/804, 1.5; 219/10.79, 10.87, 10.55 R; 600/10

[56] References Cited

U.S. PATENT DOCUMENTS

| | | | |
|---|---|---|---|
| 2,044,257 | 6/1936 | Patzohd et al. | 128/804 |
| 2,130,758 | 9/1938 | Rose | 128/804 |
| 4,028,518 | 6/1977 | Boudouris et al. | 128/804 X |
| 4,672,980 | 6/1987 | Turner | 128/804 |
| 4,702,262 | 10/1987 | Andersen et al. | 128/804 |

FOREIGN PATENT DOCUMENTS

| | | | |
|---|---|---|---|
| 1177895 | 11/1984 | Canada | 128/804 |
| 807349 | 1/1937 | France | 128/804 |
| 425803 | 3/1935 | United Kingdom | 128/804 |

OTHER PUBLICATIONS

Raskmark et al., "Focused Electromagnetic ... Tissue", IEEE Trans, MTT-32, No. 8, Aug. 1984, pp. 887–888.
Rutter et al., "A Three Dimensional Model ... ", Int. J. Hyperthermia, 1986, vol. 2, No. 3, pp. 243–252.
Lagendik, "A New Coaxial TEM ... " J. Microwave Power, 1983, 18, pp. 367–375.
Harrison et al., "Comparison . . . Hyperthermia", J. Microwave Power, 1985, pp. 1–8.

*Primary Examiner*—Lee S. Cohen
*Attorney, Agent, or Firm*—Poms, Smith, Lande & Rose

[57] ABSTRACT

An electrostatic deep heating applicator deposits RF energy in a relatively uniform manor throughout a given cross-section of the human torso, thus resulting in a similar uniform heating of the region. The applicator uses a pair of identical, rectangular, flat or cylindrical applicators which generate a heat-producing electric field predominantly parallel to the major axis of the body so as to minimize excessive surface heating. The applicator finds particular use in the treatment of deep seated cancers in patients. It need only be placed near the torso for satisfactory operation, thus allowing a relatively large air gap between it and the patient. It requires very minimum set-up time, is convenient to use and is non-threatening to the patient.

8 Claims, 10 Drawing Sheets

SAR DISTRIBUTION, 4-PLATE APPLICATOR

SAR DISTRIBUTION - 2 PLATE APPLICATOR

TEMPERATURE VS DEPTH-OF-PENETRATION IN A LIVE PIG, HEATING WITH 3-PLATE APPICATOR

ELECTROSTATIC DEEP HEATING APPLICATORS

RELATED APPLICATION DATA

This application is a continuation-in-part of co-pending U.S. patent application Ser. No. 006,219, filed Jan. 23, 1987 in the name of William H. Harrison, and entitled "Electrostatic Deep Heating Applicator."

FIELD OF THE INVENTION

The present invention relates generally to hyperthermia treatment of tumors and specifically to the selective and uniform depositing of RF energy during such treatment.

BACKGROUND OF THE INVENTION

Heating of cancerous tumors is now recognized as a valuable adjunct to the long established treatment with chemotherapy or radiotherapy because the treatment effectivity is often enhanced when hyperthermia is included as part of the protocol. It is thus desirable to elevate the tumor temperature as much as possible without causing injury to healthy tissue during the hyperthermia treatment.

Effective heating of a tumor deep within the body, say at 8 to 10 cm depth, has been a goal of many applicator designers. This is very difficult to achieve, however, and is always limited by the allowable temperature elevation of healthy tissue at lessor depths as well as at the muscle-fat interface or at the surface itself.

Figure 1:
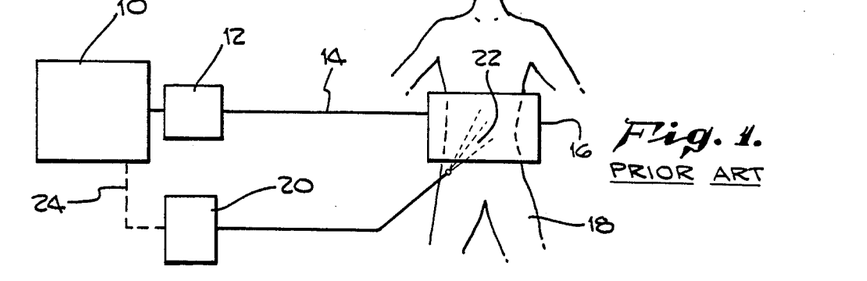
FIG. 1 is a schematic block diagram of a prior art hyperthermia system designed to heat the torso of the body.

An overview of a prior art hyperthermia system used to heat tumors in the torso of the body is illustrated in the block diagram of FIG. 1. An RF power source 10 typically provides 400-1000 watts, which is coupled via a matching network 12 and a transmission line 14 to the applicator 16, thence to the torso of the patent 18. Thermometry equipment 20 is connected to the patient to monitor temperature at various locations via fiber-optic probes 22. This thermal information can also be used to control the amplitude of the RF power source through a feed back loop 24 if desired.

Figure 2:
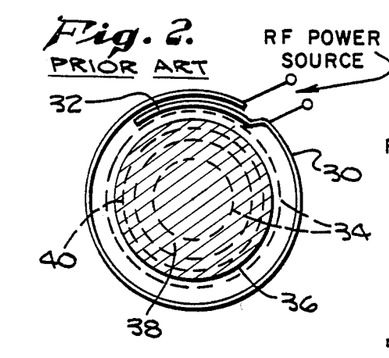
FIG. 2 is a cross-sectional view of a prior art applicator employing a single turn resonant cylinder with a magnetic induction technique of heating the torso.
Figure 3:
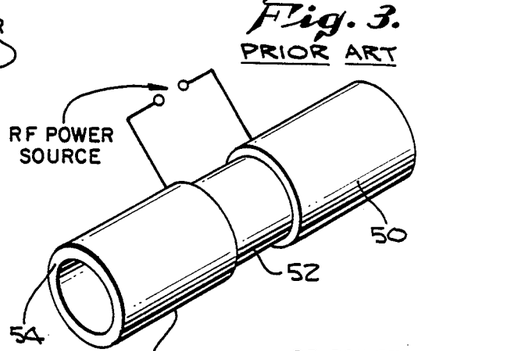
FIG. 3 is a perspective view of a prior art applicator employing two close fitting sleeves where the diameter and frequency of operation are chosen to establish a reinforced radial standing wave in the center of the phantom being treated.
Figure 4A:
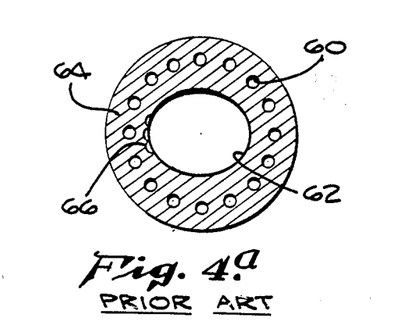
FIGS. 4(a) and (b) illustrate a prior art applicator using a series of radial dipole elements inserted in water bags that are in contact with the patient.
Figure 4B:
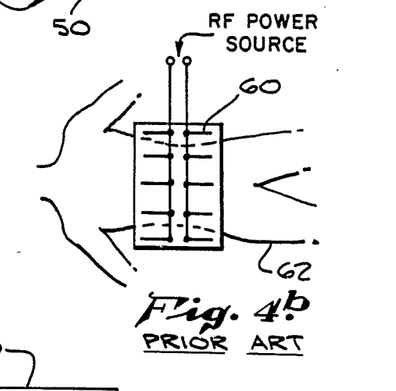

Various applicators have been successfully devised to heat tumors. However, heating has most consistently been achieved in surface or near surface tumor therapy where the overlying tissue is not a basic limitation. The design of applicators for this type of therapy are relatively straightforward and often operate at microwave frequencies where some focussing can be achieved. Other applicators that are more specifically designed for deep heating have also been developed. These devices generally operate in the lower HF or VHF frequencies where greater depth of penetration is possible. Several relevant devices of this type are illustrated in FIGS. 2, 3, and 4, and discussed in the literature.

They are:

1. "Deep Heating Electrode," Harrison, U.S. Pat. No. 4,186,729;
2. "Focused Electromagnetic Heating of Muscle Tissue," IEEE Trans. MTT-32, #8, August, 1984, pages 887-888;
3. "Annular Phased Array," IEEE Trans. BME-31, pages 106-114, January, 1984;
4. "A Three-Dimensional Model For The Coaxial TEM Deep-Body Hyperthermia Applicator," Int.J-.Hyperthermia, 1986, Vol. 2, No. 3, pages 243-252; and
5. "A New Coaxial TEM Radiofrequency/Microwave Applicator For Non-Invasive Deep-Body Hyperthermia," Journal of Microwave Power, 1983, 18, pages 367-375.
6. "Capacitor Electrodes for Shortwave Diathermy", Hyperthermia in Cancer Therapy, G. K. Hall Medical Publishers, pp 284-287.
7. "Comparison of Deep-Heating Electrode Concepts for Hyperthermia", J. Microwave Power 1985, pp 1-8
8. "Resonant Ridged Waveguide Structure Operating at 27 MHz." U.S. Pat. No. 4,282,887.

These devices are capable of penetrating the subcutaneous layers and heating imbedded tumor tissue without serious surface overheating. However, each has its limitations.

1. The patent entitled "Deep Heating Electrode," U.S. Pat. No. 4,186,729, illustrated in FIG. 2 consists of a single turn, resonant, non-contacting cylinder 30 that surrounds the body and does not require bolus (water bags) between the electrode and the patient. The conducting sheet forms the inductor 30 and the overlapping sheets form the capacitor 32 required to resonate the circuit. The device typically operates on the lower ISM frequencies, i.e., 13.56, 27.12 or 40.68 MHz. When fed from an RF power source, the resulting induced concentric electric field lines 34 are parallel to the body surface 36 and energy deposition in the deep muscle tissue 38 is not dependent upon electric field lines that must pass through the fat/skin layer 40. Clinical experience with over 1000 patients shows that excessive surface heating is spared and deep heating is often achieved.

However, the concentric electric field strength is proportional to the radius, thus heating is also dependent upon the relative radial location. Calculations and experience have shown that the half-power depth of penetration is typically 6 to 7 cm below the surface of the torso with a patient having a 1 to 2 cm fat layer.

2. The paper "Focused Electromagnetic Heating of Muscle Tissue, MTT-32" describes an applicator, as shown in FIG. 3, that consists of two identical metallic cylinders 50 spaced from one another and placed concentrically over a cylindrical phantom simulating muscle tissue 52 to be heated. A very thin 2 mm insulator 54 is placed between the phantom and the metallic cylinders. The cylinder diameter, phantom dimensions and frequency of operation are chosen to obtain constructive interference in the central region of the limb/phantom to be heated. For the case cited in this paper, this approach requires an RF power source operating at a frequency of 150 MHz.

The concept is acceptable when working with an experimental uniform cylindrical phantom 52 as shown in FIG. 3. However, the approach has serious limitations when dealing with the shape irregularities of a human torso where the required minimum spacing to the body cannot be maintained and this compromises the necessary radial phase relationship. As discussed therein, a 10 cm diameter phantom was used, with just 2 mm spacing between the phantom and the cylindrical metallic shells, i.e., a very precise spacing not achievable in a clinical environment.

3. The device in the paper "Annular Phased Array," is illustrated in FIG. 4 and consists of a group of as many as 16 dipole elements 60 that are radially spaced around the patient's torso 62 and fed in phase from a common RF source. To obtain sufficient RF coupling to the body, distilled water bags 64 are placed between the dipoles and the patient. This allows the dipole elements to function in a medium having a dielectric constant similar to muscle tissue (approximately 78), thus enhancing the coupling and minimizing the discontinuity between the dipole elements and the body surface. By carefully filling all the voids 66 between the dipole elements and the patient with water bags, efficient RF energy transfer and heating can be achieved at depth.

From a human usage point of view, this device also has serious limitations. It is very difficult to achieve uniform filling of the voids around the patient with water bags. Variable fat thickness, with its lower dielectric constant, also creates additional discontinuities. When these variations occur, localized hot spots will exist that can cause injury or limit the extent of energy input possible without localized thermal damage. It is also very time consuming to properly position the water bags and check for localized heating before treatment begins, thus contributing to patient fatigue and degraded treatment tolerance.

4. The device disclosed in the paper "A Three-Dimensional Model For The Coaxial TEM Deep-Body Hyperthermia Applicator" develops a very detailed three dimensional mathematical model showing that deep heating is possible using a pair of cylindrical sleeves as described above. This reinforces the theoretical reasons why the present invention functions well. It concludes, "For an efficient electromagnetic coupling, a sufficiently cooled water bolus between the aperture and the human body is necessary".

5. The device disclosed in the paper "A New Coaxial TEM Radiofrequency/Microwave Applicator For Non-Invasive Deep-Body Hyperthermia" provides a limited theoretical evaluation of the same model showing that the applicator will work with human body dimensions and verifies these predictions with a small model operating at an appropriately scaled higher frequency. It also requires the use of a water bolus. The paper concludes, "To match the patient to the applicator aperture, a distilled water bolus between the patient and the applicator aperture is necessary".

Figure 13:
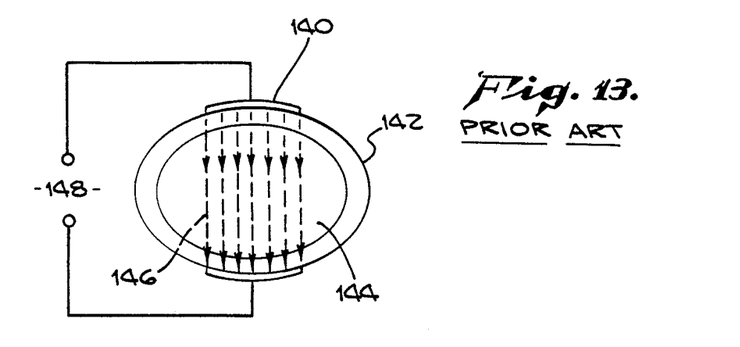
FIG. 13 is a cross sectional view of a prior art applicator employing a pair of conductive plates placed on opposite sides of the torso to be heated.

6. The device described in the paper "Capacitor Electrodes for Shortwave Diathermy," as shown in FIG. 13 illustrates the serious theoretical and practical limitations of employing either contacting or noncontacting plates 140 when heating a phantom (skin/fat 142 and muscle 144) with RF energy 148. The resulting E-field lines 146 and current flow are perpendicular to the body surface. Thus the current path is in series with the fat and muscle resulting in the higher resistance fat being seriously over heated.

Figure 14:
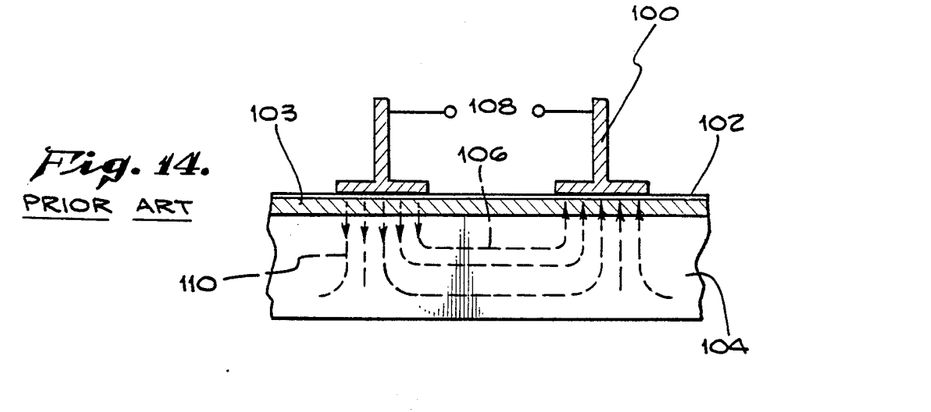
FIG. 14 is a cross sectional view of a prior art applicator employing two small conductive plates placed side by side on or near the torso to be heated.

This article further describes that shown in FIG. 14 where two small plates 100 (in terms of body size) are placed on the same surface of the patient 102. They produce currents flowing between them 106 and through the fat 103 and muscle tissue 104. But also a large perpendicular current flow 110 passes through the fat 103 causing surface overheating. This reference and discussion is included to clearly distinguish this approach from that of the present invention. The present invention, to be described, employs large plates, in terms of body size and they form a resonant aperture by which longitudinal E-field energy is transferred.

7. The article "Comparison of Deep Heating Electrode Concepts for Hyperthermia" further discusses the use of opposing plates and their limitations and also provides depth of penetration details for various applicators.

Figure 15:
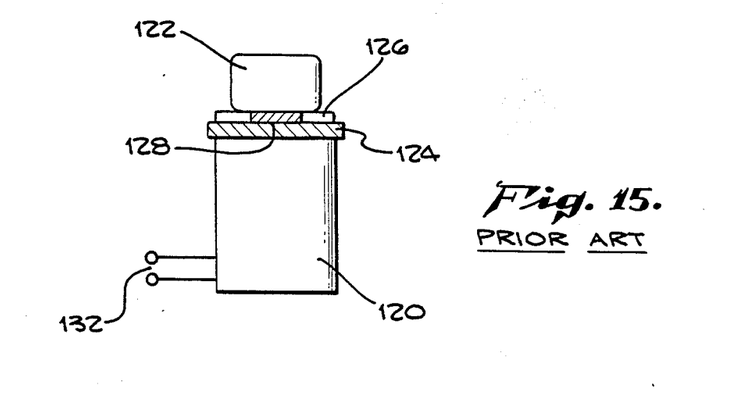
FIG. 15 is a side view of a prior art water loaded ridge waveguide applicator that must be used in conjunction with several water bags positioned between the applicator and the patient.

8. U.S. Pat. No. 4,282,887 entitled "Resonant Ridged Waveguide Structure Operating at 27 MHz." describes the device depicted in FIG. 15. FIG. 15 shows a ridge waveguide structure 120 that is filled with water to increase its effective dimensions to make it resonant at 27 MHz and yet small enough to fit on the body. A rubber bag 124, filled with deionized water, fits over the waveguide opening. A second rubber bag 126 is placed over top of the first. It is filled with a saline absorption solution to prevent over heating of the fringe area around the periphery. This second bag has its center removed so that the third water cooled bag 128, employing circulating water, is placed in the void and used to cool the fat layer that is excessively heated. Energy is coupled into the body 122 via these multiple water bags. Power to the device is applied to the applicator with a coax to waveguide transition 132.

The various prior art devices described above have the limitation of being close fitting around the object heated or using a water bolus to fill the void between the applicator and object to be heated. The IJH paper concludes, "For an efficient electromagnetic coupling, a sufficiently cooled water bolus between the aperture and the human body is necessary." The JMP paper concludes, "To match the patient to the applicator aperture, a distilled water bolus between the patient and the applicator aperture is necessary."

Prior art devices 2 through 5 are not resonant devices and a serious impedance mismatch with the 50 ohm line to the RF power source will result unless a water bolus is used as described. Moreover, the lack of a resonant structure limits the frequencies which may be employed in the devices.

Additionally, in a clinical environment, it is preferable to use as simplified a device as possible and preferably a device that does not surround the patient.

Accordingly, it is the principal object of the present invention to deposit RF energy in a uniform manner in tissue.

It is another object of the present invention to treat tumors by hyperthermia treatment without the need for a water bolus or an applicator closely fitting around the patient.

Yet another object of the invention is to allow an applicator to function at various frequencies and to optimally couple the RF energy to the applicator.

A further object of the invention is to employ structures that do not surround the patient, to eliminate the need for side coupling elements and shield plates.

SUMMARY OF THE INVENTION

The present invention, in a broad aspect, includes a pair of identical metallic cylindrical or rectangular applicator sleeves spaced along the torso. The applicator sleeves are resonated with inductors.

The sleeves are well spaced from the body (radial spacing) and do not require the use of a water bolus between the applicator and the patient. This is possible because the sleeves become part of the resonant circuit employed to raise the impedance of the applicator and obtain the necessary coupling to the torso without a water bolus between the patient and applicator. The resonant circuit also becomes a part of the matching circuit that precisely matches the cylinder impedance to the 50 ohm RF power source. To work on different frequencies, it is simply necessary for the present device to be re-resonated at the new desired frequency by changing the L/C values in the circuit.

The measured thermal response of the present invention shows relatively uniform heating at depth in cross-sections equivalent to that of the human torso.

In an alternate embodiment the present invention consists of two, three or four large metallic plates, that are positioned in a non-contacting manner above and below the torso, i.e., typically spaced 3 inches from the patient. RF is connected to the plates so as to produce a longitudinal E-field within the body. They are made part of a resonant circuit with the addition of inductors. A water bolus between the plates and the patient is not required.

While the power distribution is less uniform, the use of just two plates is also very attractive because of its performance characteristics, convenience and extreme simplicity. (The plates can be placed in the table under the patient). The E-field mapping and phantom experiments show that remarkably good depth of penetration is achieved while applying power from the one surface. This configuration can be beneficial in some cases where it is desirable to limit the overall heating to a more specific region. It also completely eliminates any patient constraint incurred by positioning of surrounding applicator hardware.

Additional inductive and capacitive loading can be employed to eliminate any E-field asymmetry or resonance sensitivity. It can also be used to purposely create an asymmetry if an E-field concentration at a specific location is desired.

A beneficial method of providing uniform heating is also provided with the invention.

Other objects, features, and advantages of the present invention will become apparent from a consideration of the following detailed description and the accompanying drawings.

BRIEF DESCRIPTION OF THE DRAWINGS

FIGS. 22(a) and (b) are top and side views respectively of the 3 plate embodiment shown in FIGS. 18(a) and (b) showing placement of a pig and thermometer placement.

DETAILED DESCRIPTION

Referring more particularly to the drawings, a new applicator, as shown in FIGS. 5–9, has been developed that deposits RF energy in a nearly uniform manor throughout a cross-section of the human torso without the undesired characteristics of the previous devices described.

Figure 5:
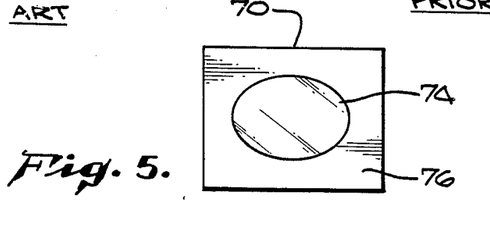
FIG. 5 is an end view of an electrostatic deep heating applicator according to the present invention.
Figure 6:
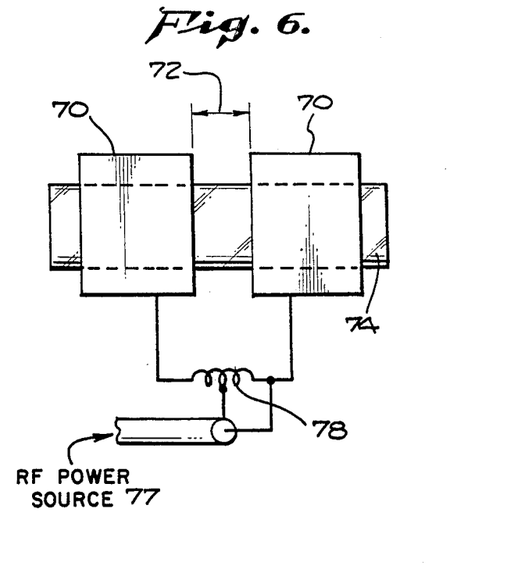
FIG. 6 is a top view of an electrostatic deep heating applicator system according to the present invention.
Figure 7:
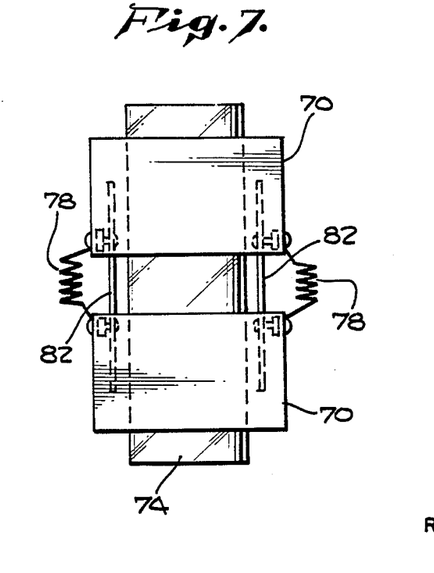
FIG. 7 is a top view showing an alternative embodiment of the present invention.

The basic applicator system and the method relating thereto, as shown in FIGS. 5 and 6, consists of two identical metallic rectangular sleeves 70, spaced from one another by a gap 72. Other shapes, such as cylindrical, elliptical, or square could be used. They are placed concentrically around the torso-simulating phantom 74. As will be shown, heating occurs principally in the gap region between the two sleeves. The sleeves dimensions (width and height) are typically 30% to 50% greater than the torso so that the applicator sleeves allow a relatively large air gap 76 to exist between the patient and the metallic sleeves.

The two sleeves 70 surrounding the torso 74 are electrically connected to each other, in the example, by a coil 78. The inductance of the coil and the capacity developed between the sleeves and the torso form a resonant circuit through which RF power 77 can be applied as shown. The RF energy can be coupled directly to the sleeves by an impedance matching circuit and a bolus, by tap coupling of the RF energy through one of the inductors, (as shown in FIG. 6) or by tap coupling of the RF energy employing the shield plates discussed below as a ground return.

Even though the sleeves surrounding the torso are small in terms of wavelength, a non-uniform E-field distribution occurs in the phantom cross-section if the two sleeves are simply resonated with an inductor attached at a single point to each sleeve as shown in FIG. 6. The resonant condition produced by the sleeve/torso capacity and inductor is also sensitive to movement and torso size.

Figures 8, 9:
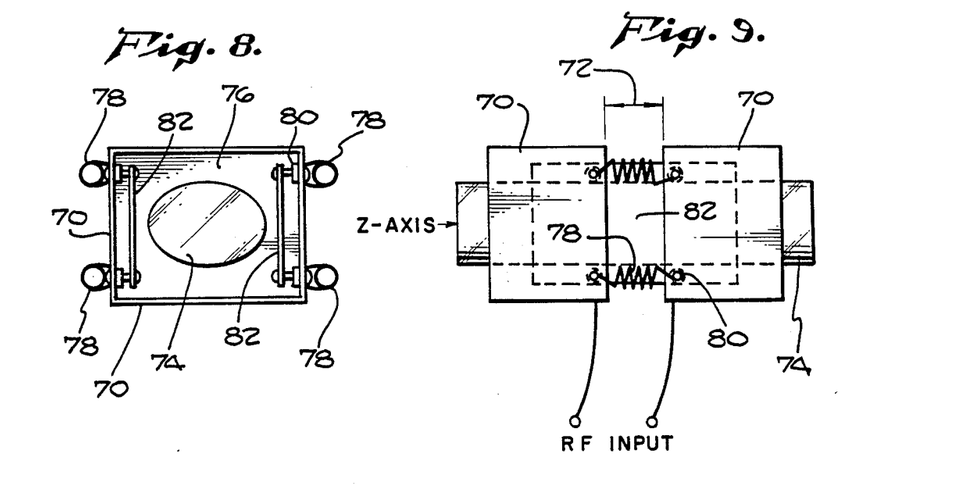
FIG. 8 is an end view of the embodiment shown in FIG. 7.
FIG. 9 is a side view of the embodiment shown in FIG. 7.

Any E-field asymmetry and resonance sensitivity can be corrected by the proper placement of additional inductive and capacitive loading as shown in the alternative embodiment of the invention depicted in FIGS. 8 and 9. The two sleeves 70 surrounding the torso 74 are electrically connected, in the figures, by four coils 78 in conjunction with eight identical capacitors 80 and two shield plates 82. The shield plates 82 are placed along both sides of the applicator between the phantom and the applicator sleeves. Electrically, the shield plate surfaces form equal capacitance to both sleeves so that a neutral RF potential exists on the shield plates, i.e., they are at ground potential. By positioning the plates as shown in the figures, the E-field level around the minor axis of the elliptical phantom was reduced to a level equal to that established elsewhere.

The addition of the coils and fixed capacitors are arranged so that the field distribution around the sleeves is very uniform. Likewise, the added capacitive loading stabilizes the resonant circuit so that it is not significantly affected by patient to patient variation.

In a prototype of the present invention, the circuit was resonated at 27.12 MHz. This frequency resulted in convenient inductor and capacitor values and good coupling to the torso was possible. Since 27.12 MHz is also an ISM frequency, its use does not require a screen room to further minimize RF radiation. The same applicator principles however can be used at other frequencies by proper choice of the circuit element values.

Figure 10:
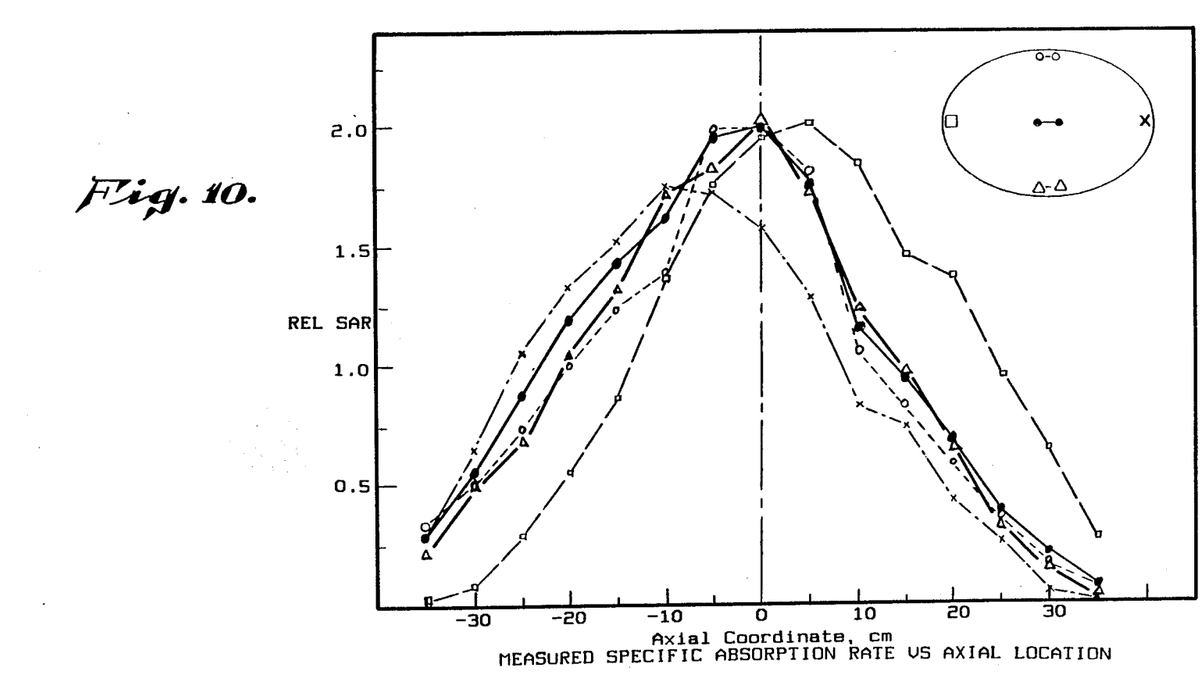
FIG. 10 is a graph showing the measured relative electric field strength in an experiment employing the present invention as observed in a saline water tank designed to simulate the cross-section and conductivity of the human torso.

The elongated elliptical cross-section phantom 74 was used to make RF E-field and thermal measurements in a saline tank with the new applicator because it more nearly duplicated the human torso. The resulting electric field pattern was measured as shown in FIG. 10. Differences in the right and left side field-strength response shape may be seen. However, since the levels did not exceed that produced in the center, it is not considered a problem.

FIG. 10 was plotted in terms of the relative Specific Absorption Rate, SAR. The tank was filled with a saline solution where the salt content was adjusted to provide the approximate conductivity of human muscle tissue at 27 MHz, i.e., 0.62 mhos per meter.

Figure 11:
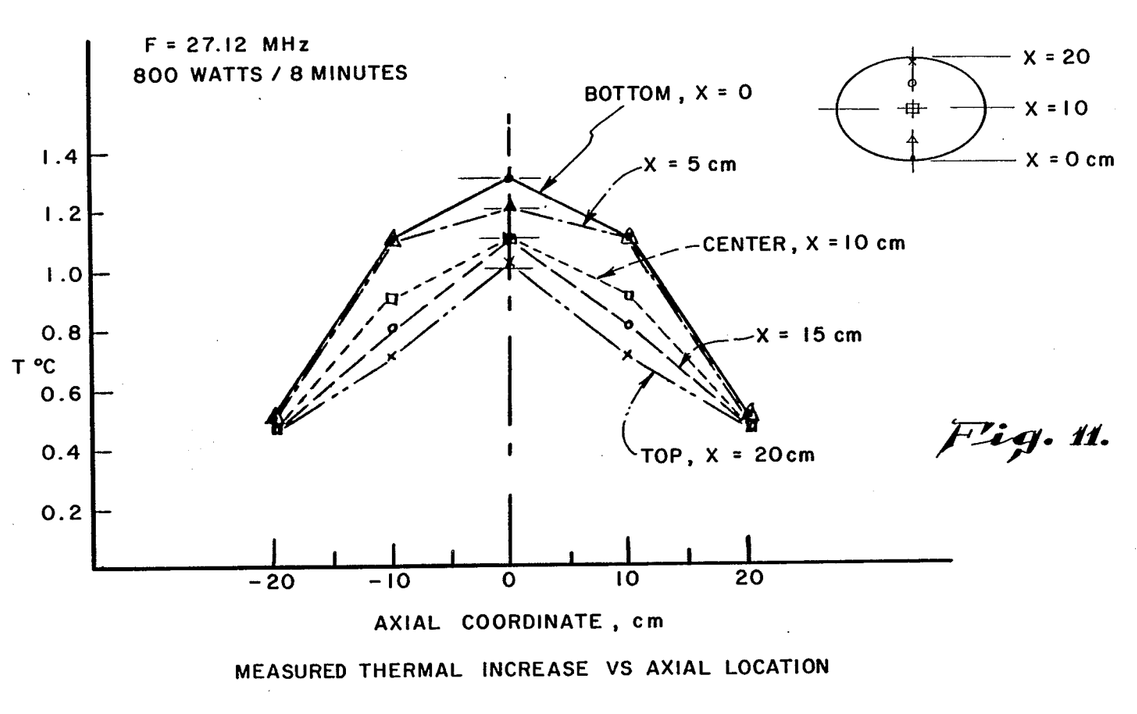
FIG. 11 is a graph showing the measured thermal pattern in an experiment employing the present invention as observed in a muscle equivalent phantom of the torso having the same cross-section as used in E-field measurements of FIG. 10.
Figure 12:
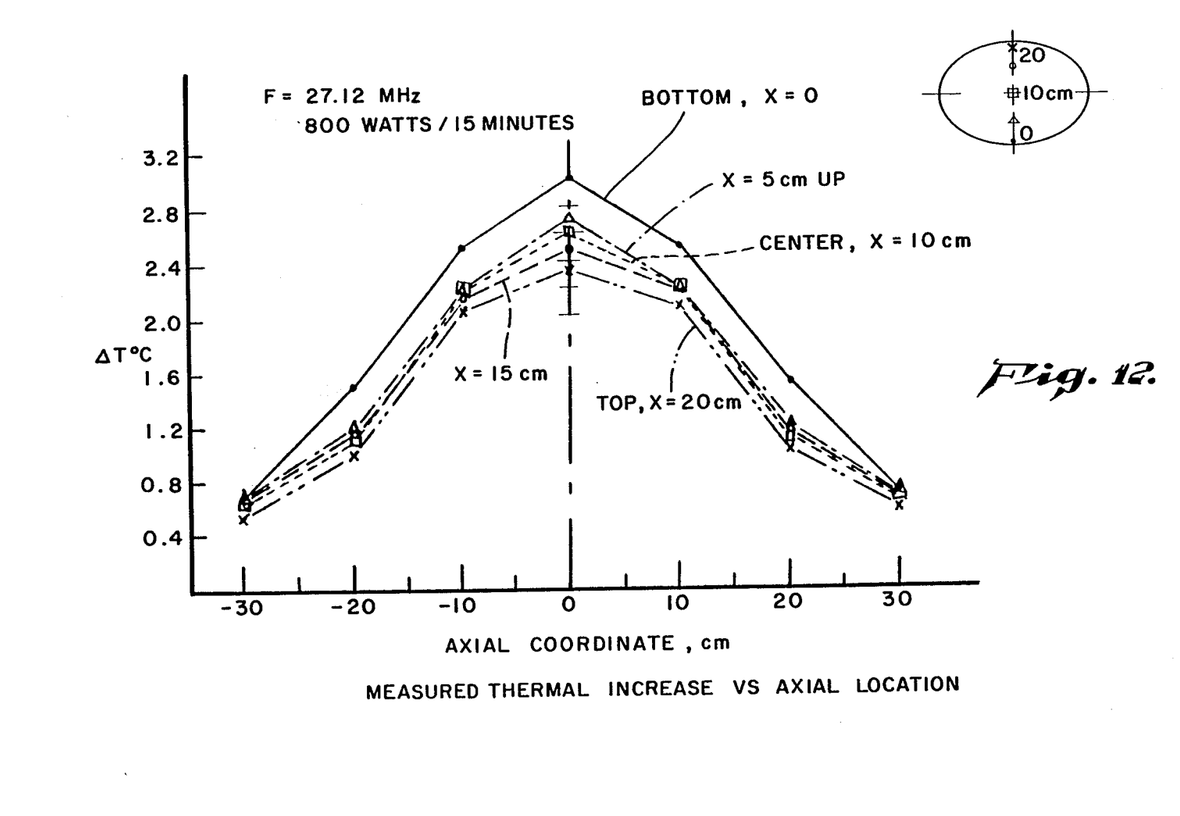
FIG. 12 is a similar measurement as that shown in FIG. 11 where the duration of heating has been increased to obtain a more pronounced temperature increase.

The corresponding heating patterns for two different heating times are shown in FIGS. 11 and 12 and the plots represent the measured thermal increase. The thermal patterns were measured in the same tank as used for the E-field measurements but with the tank filled with finely powdered silicon saturated with a saline solution. Again, the required salinity was experimentally determined, by measurement, to produce a phantom conductivity equivalent to muscle tissue.

FIG. 11 shows the thermal response after applying 800 watts for 8 minutes. FIG. 12 shows that a similar heating pattern was obtained when the duration was increased to 15 minutes. As is shown, relatively uniform heating is obtained at any depth in the desired cross-section. The thermal increase in the center of the phantom was approximately 15% less than that obtained at the bottom surface, but it was also about 10% greater than that at the top surface.

The relative SAR E-field measurements of FIG. 10 shows that a centrally located tumor (at 10 cm depth) would receive essentially the same SAR within measurement accuracy as that observed at the top and bottom surfaces, i.e., a very uniform excitation pattern that should result in a uniform heating pattern; the object of this invention.

The thermal differences noted in FIGS. 11 and 12, while minor when compared to other methods of heating, appear to be due to an inadvertent variation in the conductivity of the phantom material. Following the thermal experiments, sample conductivity measurements were made as follows: top—0.50 mhos/m, center—0.68 mhos/m and bottom surface—0.85 mhos/m.

It is important to note that maximum heating occurred in the material having the higher conductivity of muscle tissue. This characteristic is a very desireable feature since it discriminates against the heating of fat; a lower conductivity tissue that often heats excessively while attempting deep heating.

Figure 20A:
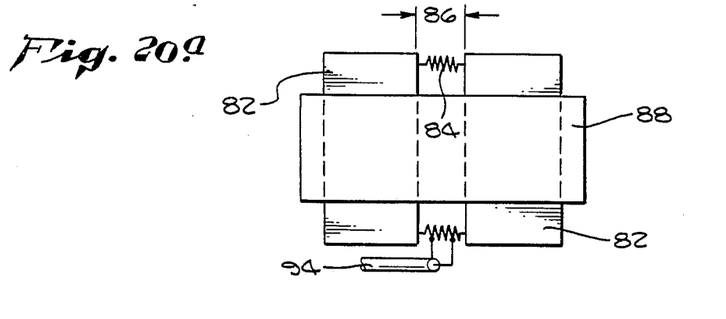
FIGS. 20(a) and (b) are top and side views respectively of an alternate embodiment of the present invention employing 2 plates.
Figure 20B:
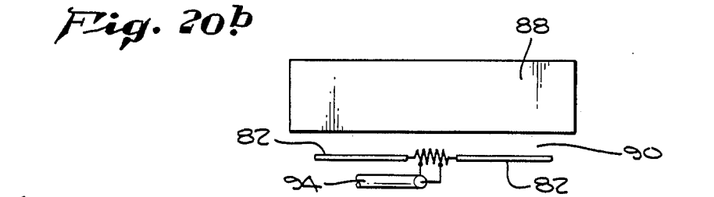

An alternate series of embodiments employing the present invention is shown in FIG. 16, 18, 20, and 22. Those shown in FIGS. 16 and 18 deposit RF energy in a nearly uniform manor throughout a cross-section of the human torso without the undesired characteristics of many devices. FIG. 20, an abbreviation of the above two applicators, forms a very convenient device that also provides deep penetration but favors the side nearest the applicator plates.

Figure 16A:
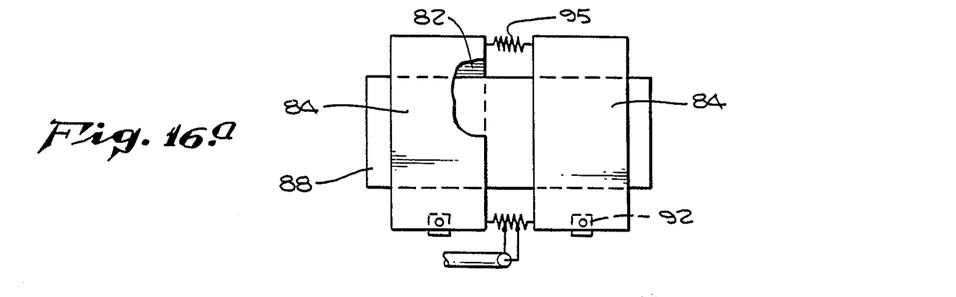
FIGS. 16(a) and (b) are top and side views respectively of an alternate embodiment of the present invention employing 4 plates.
Figure 16B:
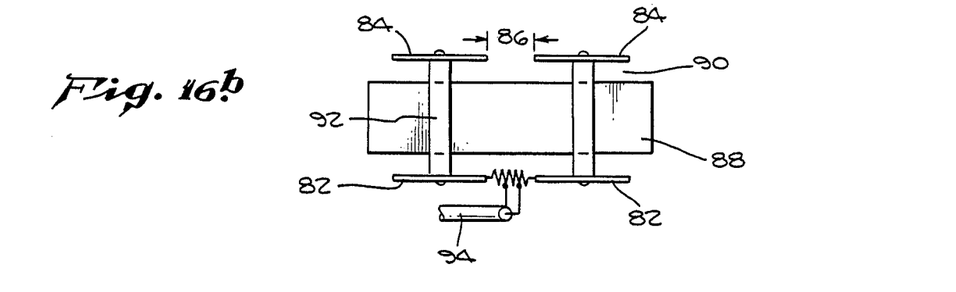

The basic applicator system and the method relating thereto of the alternate embodiment, as shown in FIG. 16, consists of four large rectangular thin metal plates 82 and 84, spaced from one another by a gap 86. They are placed above and below the torso-simulating phantom 88. The plates are 20 to 24 inches long, i.e., so as to exceed the body width. The smaller plate dimension is 10 to 12 inches. The plates are spaced 2 to 4 inches above and below the body surface 88 allowing an air gap 90. The lower plates 82 can be imbedded in the patient table. The dimensions given are typical and can be varied considerably with minor effect.

The plates become part of a resonant circuit by placing coils 95 across the gap and connecting them to the lower plates as shown. RF power is then applied via the coaxial line 94. The lower plates 82 are connected to the upper plates 84 by metal straps 92 so that they are one metallic structure. That is, the upper and lower plates are at the same RF potential. The two sets of plates 82-84 are connected by the coils 95 and RF energy is coupled to one of the coils as shown at 94. Thus the plates on opposite sides of the gap produce a difference of potential across the gap region 86 that is an aperture or RF coupling mechanism through which energy is transferred to the body. The relatively large surfaces of the plates, in terms of body dimensions, provide a large distributed capacitive coupling to the body on either side of the gap region that provides an efficient aperture through which the RF energy is launched into the body. This is further verified with measurement data.

The 4-plate version of the present invention also extends over the torso in a non-contacting manner but has no side plates as shown in FIG. 5–9. This configuration eliminates excessive side heating of elliptical shapes while still retaining the ability to produce central heating.

Figure 18A:
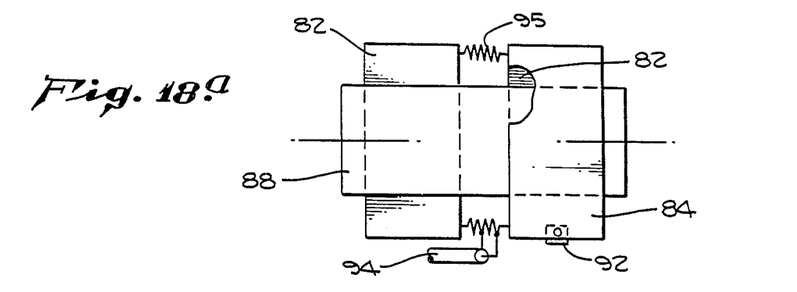
FIGS. 18(a) and (b) are top and side views respectively of an alternate embodiment of the present invention employing 3 plates.
Figure 18B:
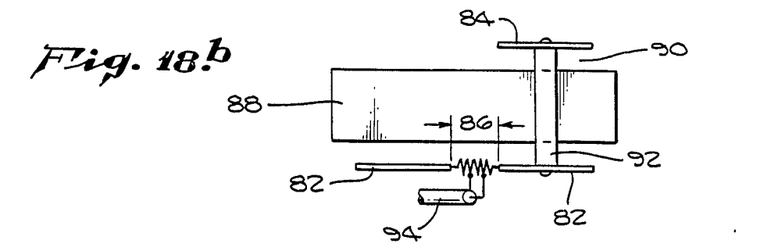

The three plate version of the present invention as shown in FIG. 18 will also produce an E-field distribution nearly as uniform as that obtained with the four plate version. Because the plates are large and extend over a significant portion of the body, the three plate version is much more convenient in a clinical setting. By removal of the one plate (that would normally protrude over the neck-nose region when heating a chest tumor), the region near the patient's face is unobstructed making the procedure much less threatening for the patient.

The two plate version of the present invention is shown in FIG. 20. Both plates can be placed in the patient table so that it is simply necessary to position the patient so that the portion to be heated is over the gap region.

Figure 17:
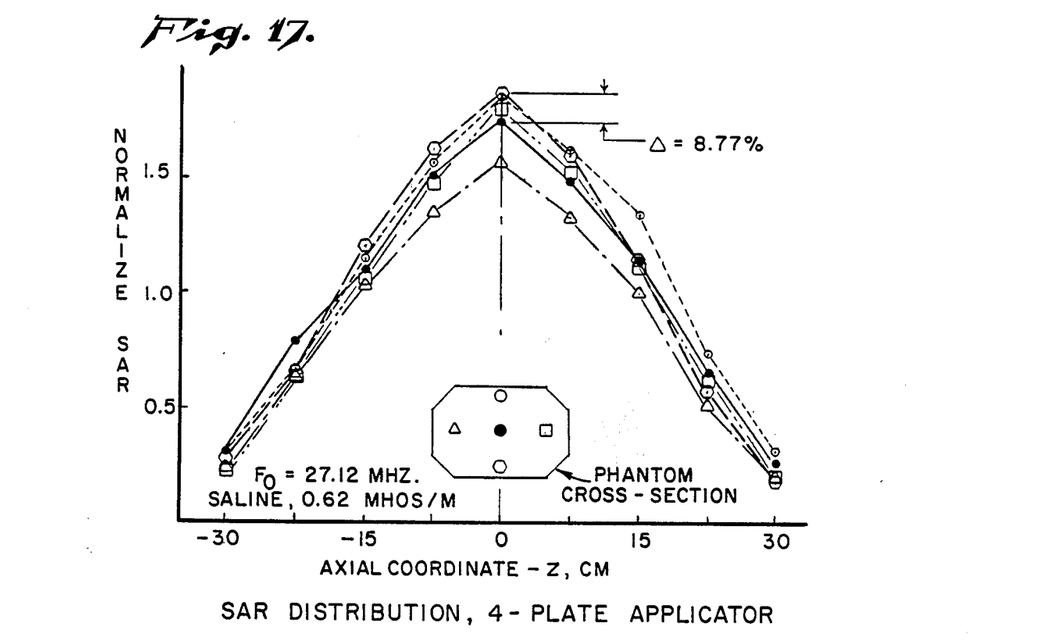
FIG. 17 shows the measured relative specific absorption rate vs location in a saline water tank phantom for the device shown in FIG. 16.
Figure 19:
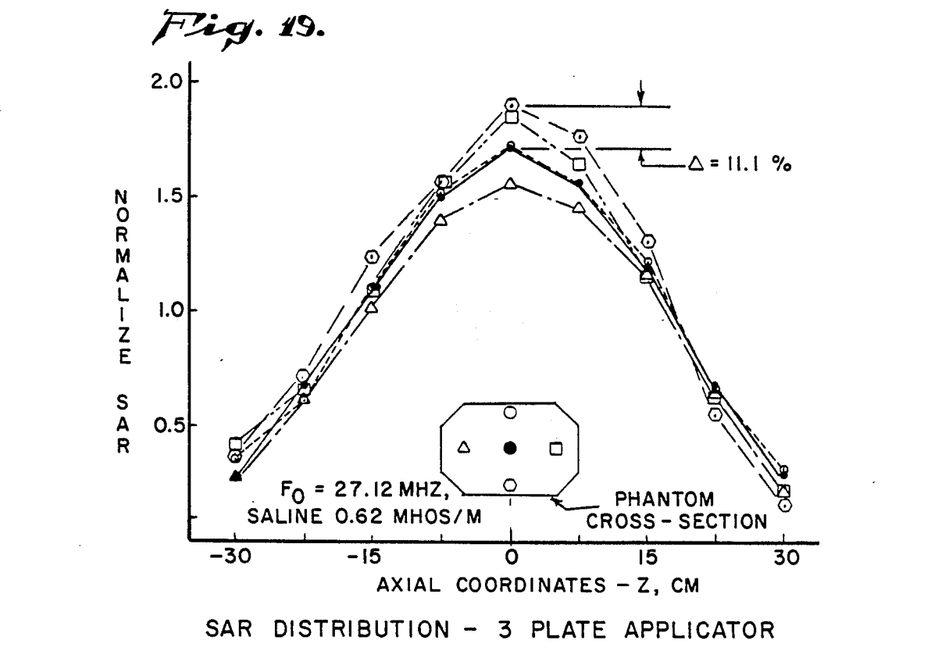
FIG. 19 shows the measured relative SAR vs location in a saline water tank phantom while using 3 plates.
Figure 21:
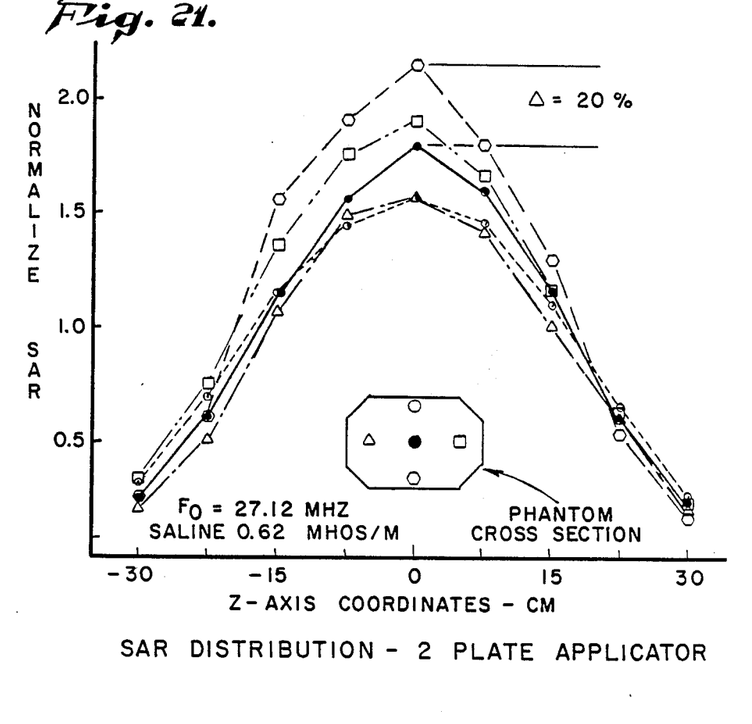
FIG. 21 shows the measured relative SAR with 2 plates mounted in the table.
Figure 22:
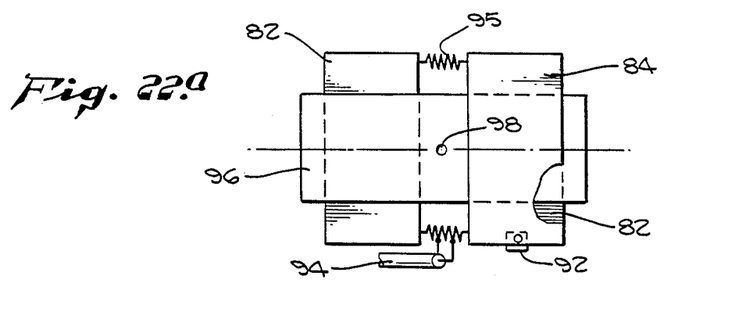

E-field intensity patterns, that are representative of the heating patterns, were measured while using the present inventions. These are shown in FIGS. 17, 19, and 21 where central heating is uniform to within 8.7% with four plates, 11.1% with three plates and 20% with the use of two plates.

Figure 23:
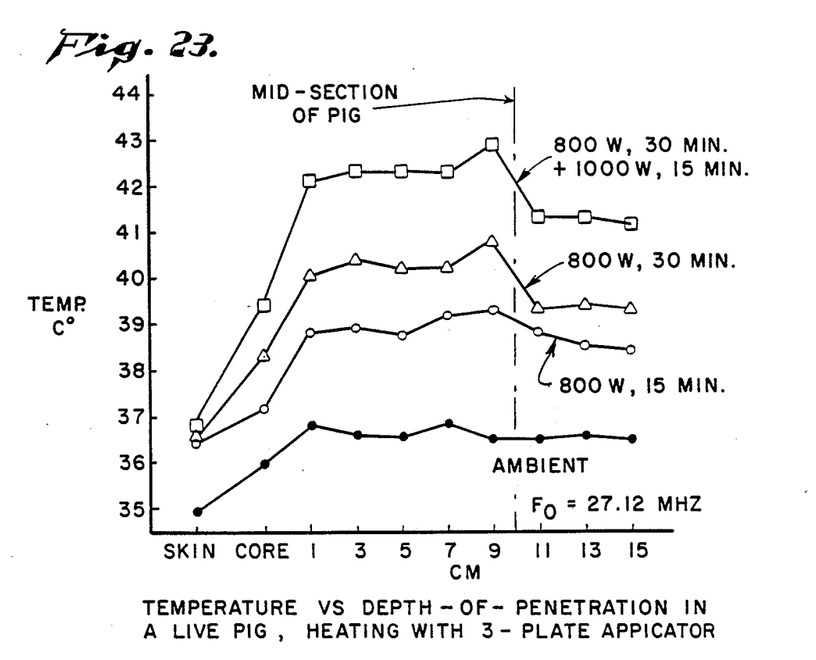
FIGS. 23 shows thermal data obtained through the midsection of a live sedated pig while using the 3 plate applicator configuration.

With reference to FIG. 23, the thermal performance of the present invention was demonstrated by heating a 125 pound sedated pig 96. The pig was placed on its side and positioned with its mid-section in the gap of the three plate version of the present invention. A catheter 98 was inserted through the mid-section into which a fiberoptic thermal probe was inserted and moved to various locations to obtain a thermal profile. Temperature measurements were made before heating and after 15, 30 and 45 minutes of heating as shown in FIG. 23. As may be seen, the upper surface (skin and thick fat layer of a pig) was not superficially heated, as would be the case if significant perpendicular E-fields were present. The thermal pattern is also remarkable uniform, especially when considering the heterogeneous body material in the cross-section. Thus the overwhelming utility of the present invention is authenticated.

In the foregoing description of the present invention, a preferred embodiment of the invention has been disclosed. It is to be understood that other mechanical and design variations are within the scope of the present invention. Accordingly, the present invention is not limited to the particular arrangement which has been illustrated and described herein.

What is claimed is:

1. An electrostatic deep heating applicator for tissue in the body comprising:
   first and second conductive plate means for forming a gap for depositing RF energy to said tissue, said first and second plate means adapted to be disposed axially along said body to form said gap, with each of said plate means and said body defining an air space of distributed capacitive reactance such that said applicator is loosely coupled to said tissue;
   inductor means, attached to said first and second plate means and adapted to be coupled to a source of RF energy, for resonating the resonant circuit defined by said first and second plate means, said capacitive reactance, said body, and said inductor means to establish an electric field across said gap and currents in said tissue; and
   control means, connected to said first and second plate means, for effecting uniformity in the energy distribution over the surface area of said first and second plate means and thereby of said electric field in said gap to cause preferential and uniform heating in said gap.

2. An applicator as defined in claim 1, wherein said first and second plate means each comprises two generally flat and rigidly interconnected metallic plates disposed in opposing relation.

3. An applicator as defined in claim 1, wherein said first and second plate means each comprise at least a pair of curved and rigidly interconnected metallic plates.

4. An applicator as defined in claim 1, wherein said inductor means includes means for coupling said RF energy to said plate means.

5. An applicator as defined in claim 4 wherein said means for coupling comprises an impedance matching circuit adapted to be coupled between said resonant means and said RF energy source.

6. An applicator as defined in claim 1, wherein said first and second plate means each comprise a generally flat plate disposed in linear relation.

7. An applicator as defined in claim 1, wherein said first plate means comprises a pair of rigidly interconnected flat plates disposed in opposing relation and said second plate means comprises a third plate adjacent one of said flat plates.

8. An applicator as defined in claim 13, wherein said control means comprises second inductor means connected to said first and second plate means.

* * * * *